United States Patent
Inamoto et al.

(10) Patent No.: US 6,922,247 B2
(45) Date of Patent: Jul. 26, 2005

(54) AUTOMATIC OPTICAL MEASUREMENT METHOD

(75) Inventors: Naoki Inamoto, Kumamoto (JP); Yoshimi Sawamura, Kyoto (JP); Shinji Fujimura, Shiga (JP); Kunikazu Taguchi, Hirakata (JP)

(73) Assignee: Otsuka Electronics Co., Ltd., Osaka (JP)

( * ) Notice: Subject to any disclaimer, the term of this patent is extended or adjusted under 35 U.S.C. 154(b) by 151 days.

(21) Appl. No.: 10/333,990

(22) PCT Filed: Jul. 26, 2001

(86) PCT No.: PCT/JP01/06437

§ 371 (c)(1),
(2), (4) Date: Jan. 27, 2003

(87) PCT Pub. No.: WO02/10717

PCT Pub. Date: Feb. 7, 2002

(65) Prior Publication Data

US 2003/0147081 A1 Aug. 7, 2003

(30) Foreign Application Priority Data

Jul. 28, 2000 (JP) ........................................ 2000-229518
Aug. 1, 2000 (JP) ........................................ 2000-233392

(51) Int. Cl.[7] ............................................. G01N 21/55
(52) U.S. Cl. ...................................................... 356/448
(58) Field of Search ................................ 356/445–448, 356/434

(56) References Cited

U.S. PATENT DOCUMENTS

| 3,813,146 | A | * | 5/1974 | Burch et al. ................ 356/434 |
| 3,960,077 | A | * | 6/1976 | Aylett ......................... 356/448 |
| 4,029,419 | A | * | 6/1977 | Schumann et al. ......... 356/448 |
| 4,666,309 | A |   | 5/1987 | Barry et al. |
| 4,830,504 | A | * | 5/1989 | Frohardt et al. ............ 356/448 |
| 5,040,889 | A |   | 8/1991 | Keane |
| 6,040,902 | A |   | 3/2000 | Jung et al. |

FOREIGN PATENT DOCUMENTS

| EP | 0296956 A2 | 12/1988 |
| JP | 2000-199743 | 7/2000 |
| WO | WO 96/27783 | 9/1996 |

OTHER PUBLICATIONS

S. Tadashi, "Measuring Instrument For Absolute Reflection Factor In Ultraviolet Range,:" Patent Abstract of Japan of JP01013438 (Jan. 18, 1989).

* cited by examiner

Primary Examiner—Richard A. Rosenberger
(74) Attorney, Agent, or Firm—Finnegan, Henderson, Farabow, Garrett & Dunner, L.L.P.

(57) ABSTRACT

In an automatic optical measurement method according to the invention, with a movable reflection plate 6 moved to place under an optical axis, light projected from a light projecting portion 3a is received by a light receiving portion 3b via the movable reflection plate 6, a stationary reflection plate 11 and the movable reflection plate 6, whereas with the movable reflection plate 6 moved away from the optical axis and a reference 8 set on a sample stage 10, light projected from the light projecting portion 3a is received by the light receiving portion 3b via the reference 8 whereby a ratio between the intensities of the received lights is determined. During a sample measurement, light projected from the light projecting portion 3a with the movable reflection plate 6 moved to place under the optical axis is received by the light receiving portion 3b via the movable reflection plate 6, stationary reflection plate 11 and movable reflection plate 6 so that the intensity of light thus received and the above ratio are used for estimating an intensity of light to be measured with the reference, the estimated intensity of light being used for correcting an intensity of light received via a sample.

3 Claims, 5 Drawing Sheets

AUTOMATIC OPTICAL MEASUREMENT METHOD

TECHNICAL FIELD

The present invention relates to an automatic optical measurement method including a light projecting portion and a light receiving portion and adapted to project light from the light projecting portion onto a sample for measurement of light reflected therefrom.

BACKGROUND ART

In a case where measurement is taken on the light reflectivity or light transmittance of a plurality of samples being carried, measurement errors may result from the variations of ambient temperature, intensity of light source, sensitivity of a detector, curvature of an optical fiber and the like, which will occur during a sample measurement. Hence, a reference measurement is performed prior to the conveyance of the samples or at a regular suspension of the conveyance of the samples during the measurement. The reference measurement is taken on a reference reflection element, which is set in a light path of an optical measurement system. This provides for improved measurement accuracies of the whole measurement system including the light source and the detector.

In order to regularly set the reference reflection element as reference in the measurement light path, however, a mechanism for automatically conveying the reference reflection element is required in addition to the sample conveyance mechanism. This results in an complicated configuration and an increased cost of the measurement system. Furthermore, the samples must be removed for allowing the reference reflection element to be set to place and then be re-placed at individual places after the reference measurement. This process consumes a part of the time for the sample measurement, resulting in a reduced time for the sample measurement. As a result, the time is used at a lowered efficiency.

DISCLOSURE OF THE INVENTION

In view of the foregoing, it is an object of the invention to provide an automatic optical measurement method (1) and (2) which provide for an estimation of a reference light intensity without setting the reference reflection element in the measurement light path, thereby achieving increased measurement accuracies.

(1) In an automatic optical measurement method according to the invention, a movable reflecting member is movably disposed at place between a sample stage and a light projecting and receiving portions; a stationary reflecting member is disposed on an opposite side of the movable reflecting member from the sample stage; with the movable reflecting member moved to place under an optical axis, light projected from the light projecting portion is received by the light receiving portion via the movable reflecting member, stationary reflecting member and movable reflecting member; with the movable reflecting member moved away from the optical axis, a reference is set on the sample stage so as to allow the light receiving portion to receive light from the light projecting portion via the reference, whereby a ratio between the intensities of the received lights is determined; and during a sample measurement, light projected from the light projecting portion with the movable reflecting member moved to place under the optical axis is received by the light receiving portion via the movable reflecting member, stationary reflecting member and movable reflecting member so that an intensity of the received light and the ratio are used for estimating an intensity of light to be measured with the reference set to place, the estimated intensity of light being used for correcting an intensity of light received via a sample.

According to the above method, the ratio between the intensities of the received lights measured using the movable reflecting member, stationary reflecting member and reference provides a system-specific constant free from the system variations including the variations of ambient temperature, intensity of light from a light source, sensitivity of a detector, a curvature of an optical fiber or the like.

During the sample measurement, the intensity of light measured with the reference set to place can be estimated using, in combination with the ratio, the intensity of light measured using the movable reflecting member and the stationary reflecting member. The estimation of a reference light intensity provides a value corresponding to the system variations at a measurement time.

The use of the estimation of a reference light intensity permits a sample light intensity to be measured without being affected by the system variations.

As described above, the automatic optical measurement method of the invention permits the reference light intensity to be estimated during the sample measurement without setting a reference reflection element as reference to place in the measurement light path. Hence, despite the variations of ambient temperature, intensity of light from the light source, sensitivity of the detector, curvature of the optical fiber and the like, a correct measurement can be taken on the sample light intensity. This results in increased sensing accuracies of the measurement system.

(2) In an automatic optical measurement method according to the invention, a transparent or translucent member is fixed in place between a sample and a space between a light projecting portion and a light receiving portion for reflecting a part of the light projected from the light projecting portion into the light receiving portion; a measurement of intensity of light taken without setting a reference in place and a measurement of intensity of light taken with the reference set in place are used for determining a ratio between an intensity of light reflected by the member and the measurement of intensity of light reflected by the reference; and a measurement of intensity of light to be taken with the reference set in place is estimated during a sample measurement by using a measurement of intensity of light taken without setting a sample in place and the ratio thus determined, the resultant estimation being used for correcting the measurement of intensity of light received via the sample.

According to the above method, the ratio between the intensity of light reflected by the member and the intensity of light reflected by the reference provides a system-specific constant free from the variations of intensity of light from the light source or sensitivity of the detector, the ratio determined using the intensity of light measured without setting the reference in place and the intensity of light measured with the reference set in place.

If during the sample measurement, the measurement of intensity of light to be taken with the reference in place is estimated using the intensity of light measured without selling a sample in place in combination with the ratio, the estimation of the reference light intensity provides a value corresponding to the variations of intensity of light from the light source or sensitivity of the detector.

Thus, the use of the estimation of the reference light intensity may provide for a measurement of sample light intensity which is free from the variations of intensity of light from the light source or sensitivity of the detector at a measurement time in question.

According to the invention, the reference light intensity can be estimated during the sample measurement without setting the reference reflection element as reference in the measurement light path. Therefore, it is ensured that a correct measurement can be taken on the sample despite the variations of intensity of light from the light source or sensitivity of the detector. Thus are achieved increased sensing accuracies of the measurement system.

Preferred embodiments of the invention will be described in detail hereinbelow with reference to the accompanying drawings.

BEST MODES FOR CARRYING OUT THE INVENTION

1. First Embodiment

Figure 1:
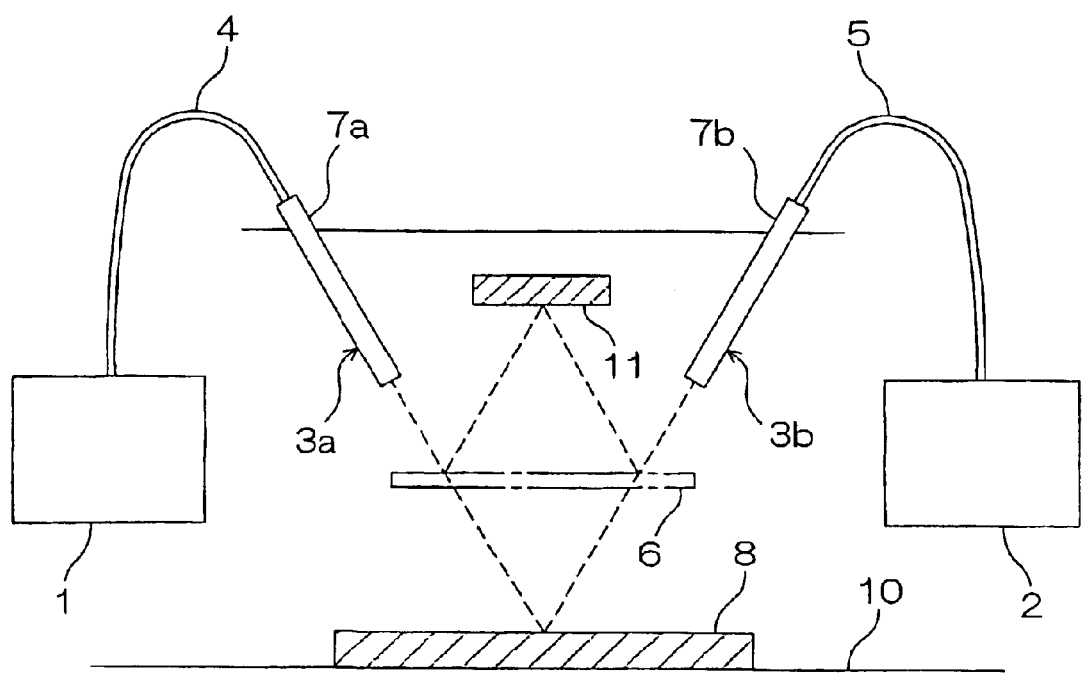
FIG. 1 is a front view showing an arrangement of an automatic optical measurement system according to a first embodiment of the invention.
Figure 2:
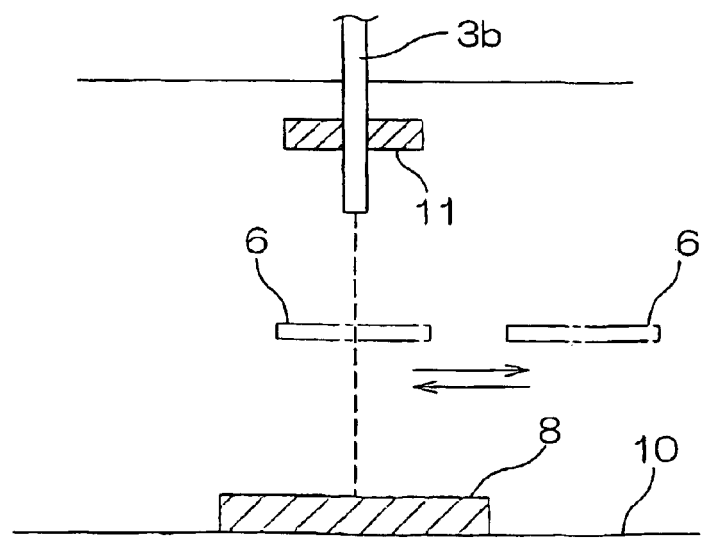
FIG. 2 is a side view showing the arrangement of the above automatic optical measurement system.

FIG. 1 is a front view showing an arrangement of an automatic optical measurement system whereas FIG. 2 is a side view showing the arrangement thereof. A light source 1 is connected with a light projecting fiber 4, a distal end of which is inserted in a metallic tube 7a. The light projecting fiber 4 and the metallic tube 7a form a fiber probe 3a. The light source 1 may be of any type that is capable of emitting light having a suitable wavelength for sample measurement, including a laser light source, candescent light source and the like.

A light receiving fiber 5 also has its distal end inserted in a metallic tube 7b. The light receiving fiber 5 and the metallic tube 7b form a fiber probe 3b. A terminal end of the light receiving fiber 5 is connected to a detector 2. A configuration of the detector 2 is not limited. For example, a photo tube, photodiode array or the like may be used as the detector. The detector 2 may be provided with a spectroscope or filter on a front side thereof.

The light projecting fiber 4 and the light receiving fiber 5 may be formed of any material such as, for example, quartz, transparent plastic and the like.

A stage 10 on which a sample or reference is placed is disposed at a place at which phantom lines extended form the distal ends of the fiber probes 3a, 3b intersect each other.

A movable mirror 6 is movably mounted in place intermediate the fiber probes 3a, 3b and the stage 10. A stationary mirror 11, facing downward, is mounted in place above the movable mirror 6.

As shown in FIG. 2, the movable mirror 6 is adapted for parallel movement between a position where optical axes of the fiber probes 3a, 3b intersect (indicated by a dot-dash line) and a position spaced away from the optical axis (indicated by a solid line). Moving means for the movable mirror 6 may employ any of the known means such as pinion and rack driven by a motor. The movable mirror may be moved manually instead of using the motor.

Now, description is made as to how the automatic optical measurement system of the above arrangement is used.

(1) Measurement at Activation of Automatic Optical Measurement System

The light source 1 is activated (turned on). As shown in FIG. 1, a reference reflection plate 8 (the reflectivity of which is known) as reference is placed on the stage 10 while the movable mirror 6 is moved in place under the optical axes. In this state, light projected from the light projecting fiber 4 is reflected by the movable mirror 6 and the stationary mirror 11 and then again by the movable mirror 6, so as to enter the light receiving fiber 5. The intensity of light incident at the light receiving fiber 5 is measured by means of the detector 2. The intensity of the incident light is defined as "M0".

Subsequently, the movable mirror 6 is moved away from the optical axes. In this state, the reference reflection plate 8 is radiated with light from the light projecting fiber 4 so as to cause the reflected light therefrom to enter the light receiving fiber 5 for measurement of intensity of the incident light. The intensity of incident light is defined as "R0".

A system constant F is determined by calculating R0/M0.

$$F = R0/M0$$

(2) Sample Measurement

Figure 3:
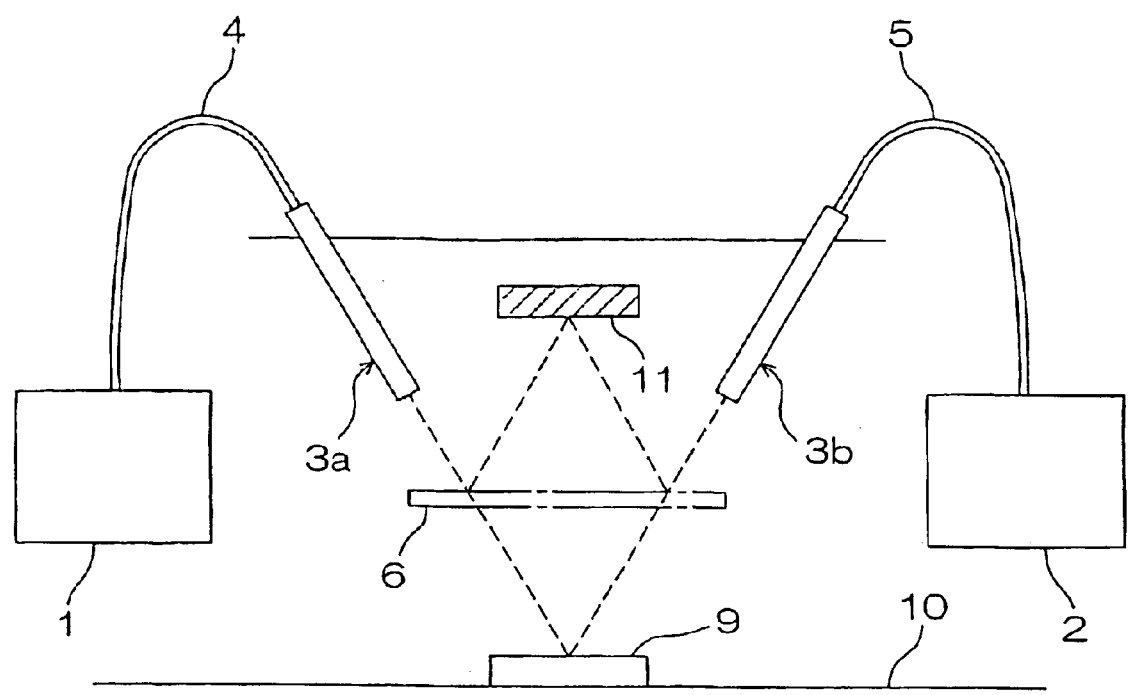
FIG. 3 is a front view showing the arrangement of the automatic optical measurement system for measuring a reflectivity of a sample 9.

FIG. 3 is a front view showing an arrangement of an automatic optical measurement system for measuring the reflectivity of a sample 9.

The movable mirror 6 is moved in place under the optical axes. In this state, the light from the light projecting fiber 4 is reflected by the movable mirror 6 and the stationary mirror 11 and then again by the movable mirror 6 so as to enter the light receiving fiber 5. The intensity of light incident at the light receiving fiber 5 is measured by means of the detector 2. The intensity of the incident light is defined as "M1".

Subsequently, the movable mirror 6 is moved away from the optical axes. In this state, the sample 9 is radiated with the light from the light projecting fiber 4 so as to cause the reflected light therefrom to enter the light receiving fiber 5 for measurement of intensity of the incident light. The intensity of incident light is defined as "S".

Using an expression S/(M1·F) a reflectivity of the sample 9, which is corrected for light intensity, can be determined.

As described above, even if the intensity of light from the light source is varied during the sample measurement, a correct measurement can be taken on the reflectivity of the sample 9 without physically setting the reference reflection plate 8 in place.

2. Second Embodiment

Figure 4:
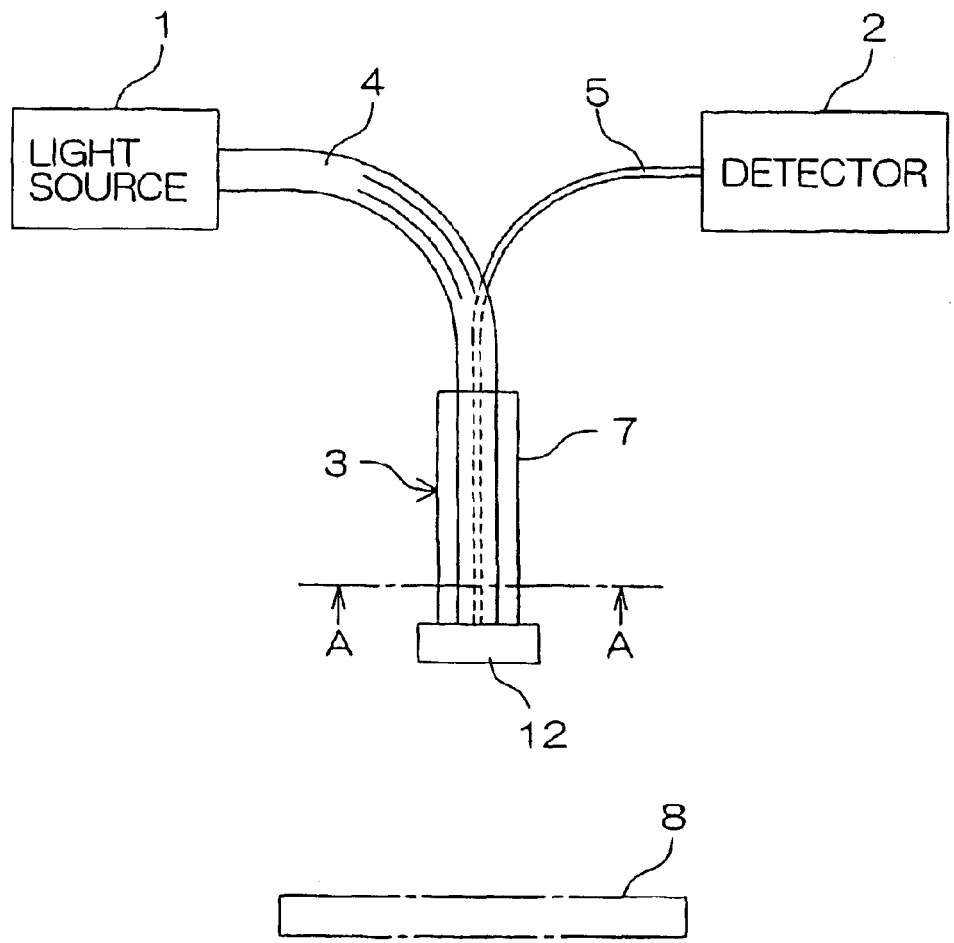
FIG. 4 is a schematic diagram showing an automatic optical measurement system according to a second embodiment of the invention.

FIG. 4 is a schematic diagram of another automatic optical measurement system of the invention. The light source 1 is connected with bundled light projecting fibers 4, distal ends of which are inserted in a metallic tube 7 along with the light receiving fiber 5. The light receiving fibers 4, light receiving fiber 5 and metallic tube 7 form the fiber probe 3. The light source 1 may be of any type that is capable of emitting light having a suitable wavelength for sample measurement, including a laser light source, candescent light source and the like. The light projecting fibers 4 and light receiving fiber 5 maybe formed of any material such as, for example, quartz, transparent plastic and the like.

A transparent plate 12 functioning as reference is secured to a distal-end face of the fiber probe 3. The transparent plate 12 may be mounted by an arbitrary method using an adhesive, screw or the like. Although the transparent plate 12 is tightly adhered to the distal-end face of the fiber probe 3, it is also possible to mount the transparent plate 12 to the fiber probe 3 via a gap therebetween.

The material for the transparent plate 12 is not limited. Examples of a usable material include quartz glass, PMMA (poly methyl methacrylate) and the like. The transparent plate 12 may be replaced by a translucent plate upon which a metallic film is deposited (half mirror).

The light receiving fiber 5 has its terminal end connected to the detector 2. The configuration of the detector 2 is not limited. For example, a photo tube, photodiode array or the like may be used as the detector. The detector 2 maybe provided with a spectroscope or filter on the front side thereof.

Figure 5:
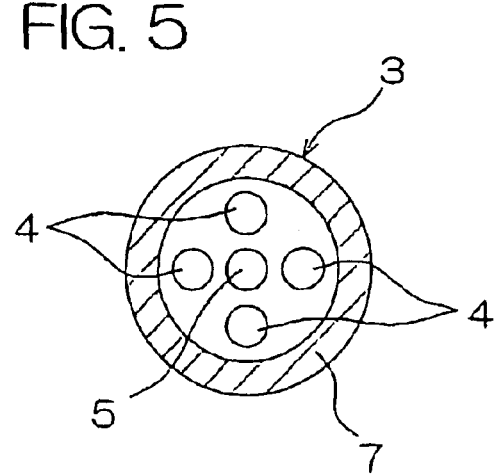
FIG. 5 is a sectional view of a fiber probe 3 taken on the line A—A in the above figure.

FIG. 5 shows an exemplary section of the fiber probe 3. One or more light projecting fibers 4 are inserted in the metallic tube 7 whereas the light receiving fiber 5 extends through the center of the tube 7. It is noted that the light receiving fiber 5 does not necessarily extend through the center of the tube but may occupy any place within the metallic tube 7 in section.

Figure 6:
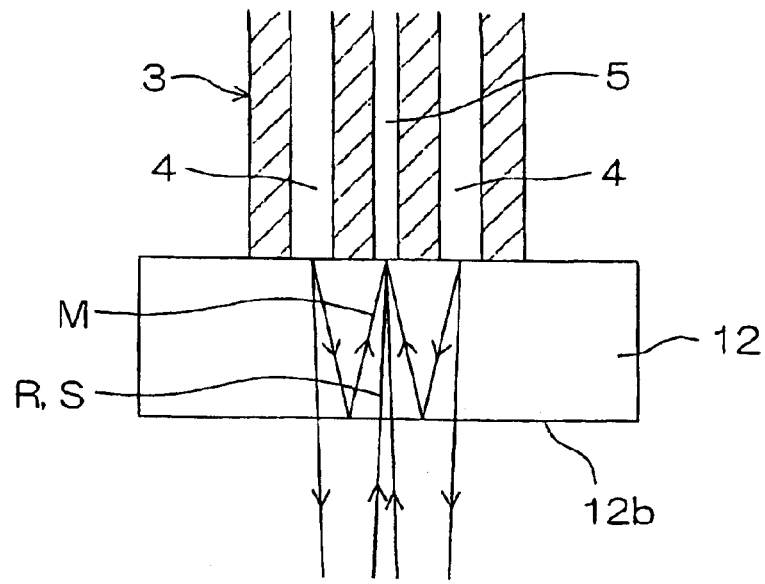
FIG. 6 is a diagram showing light paths in a transparent plate 12 tightly adhered to a distal-end face of the fiber probe 3.

FIG. 6 shows light paths within the transparent plate 12 tightly adhered to the distal-end face of the fiber probe 3. A part of the outgoing light from the light projecting fiber 4 is reflected by a bottom face 12b of the transparent plate 12 thereby to enter the light receiving fiber 5 (see a light path M). The rest of the outgoing light from the light projecting fiber 4 that passes through the transparent plate 12 is reflected by the reference reflection plate 8 or the sample 9 located under the transparent plate, so that the light thus reflected is returned to the transparent plate 12 to enter the light receiving fiber 5 (see a light path R or S).

Figure 7:
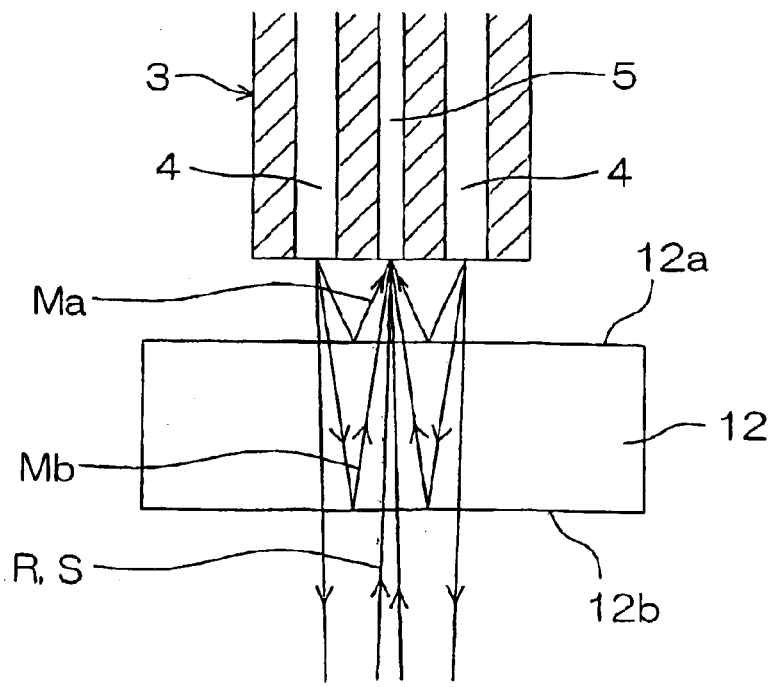
FIG. 7 is a diagram showing light paths in the transparent plate 12 spaced away from the distal-end face of the fiber probe 3.

FIG. 7 shows light paths within the transparent plate 12 spaced away from the distal-end face of the fiber probe 3. Some of the light outgoing from the light projecting fiber 4 is reflected respectively by an upper face 12a and a bottom face 12b of the transparent plate 12 to enter the light receiving fiber 5 (see light paths Ma and Mb). The rest of the outgoing light from the light projecting fiber 4 that passes through the transparent plate 12 is reflected by the reference reflection plate 8 or the sample 9, so that the light thus reflected is returned to the transparent plate 12 to enter the light receiving fiber 5 (see the light path R or S).

Now, description is made as to how the automatic optical measurement system of the above arrangement is used. In the following description, it is provided that the transparent plate 12 is designed to adhere tightly to the distal-end face of the fiber probe 3. It is noted, however, that a similar effect may be obtained by the configuration wherein the transparent plate 12 is spaced away from the distal-end face of the fiber probe 3.

(1) Measurement at Activation of Automatic Optical Measurement System

In a state where the transparent plate 12 is secured to the distal end of the fiber probe 3, as shown in FIG. 4, the light source 1 is turned on and the intensity of light M0 is measured by means of the detector 2. The intensity of light M0 is an intensity of light reflected from the transparent plate 12.

Next, as indicated by the dot-dash line in FIG. 4, the reference reflection plate 8 is set in place for taking measurement of F=M0+R0 by means of the detector 2.

Then, a net reference light intensity R0 reflected from the reference reflection plate 8 is determined by subtracting the intensity of light M0 from the intensity of light M0+R0.

A calibration constant F is determined by calculating F=R0/M0.

(2) Sample Measurement

Figure 8:
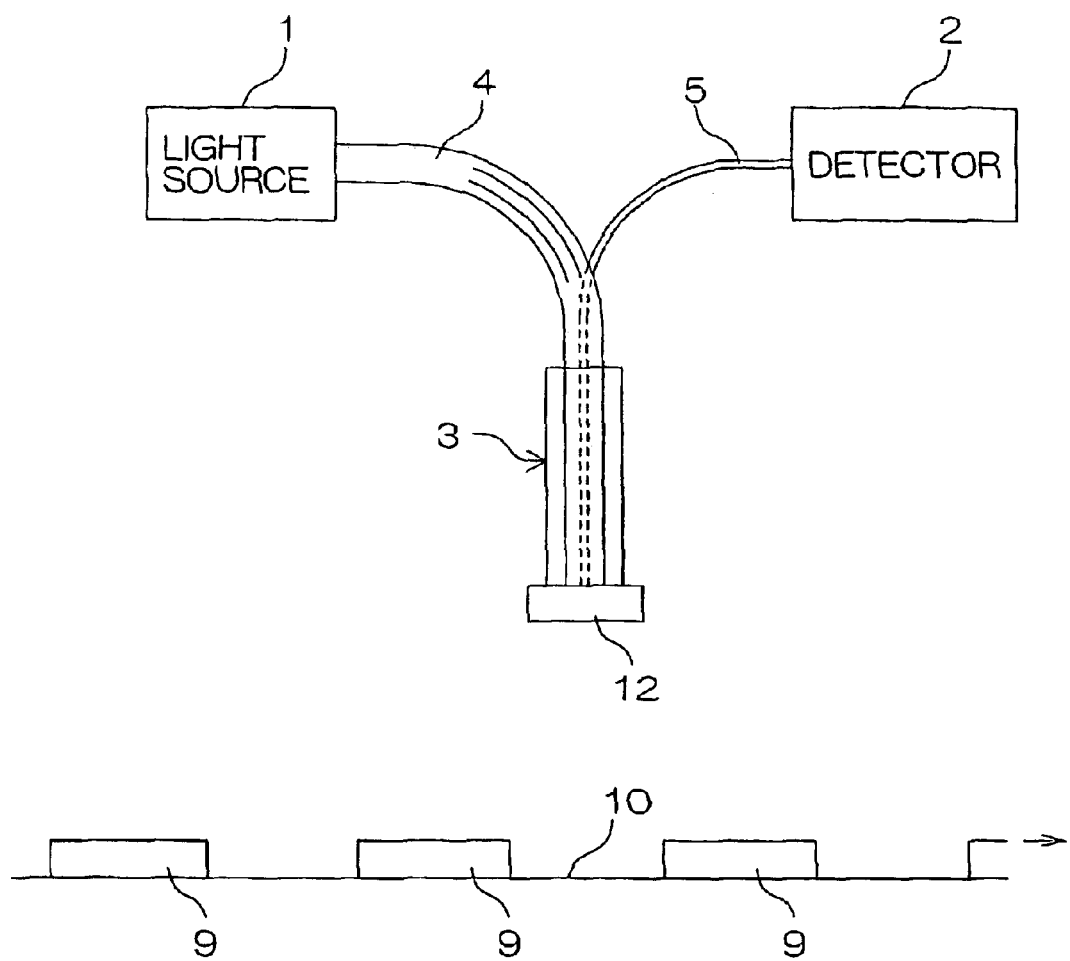
FIG. 8 is a diagram showing an arrangement of the automatic optical measurement system for measuring reflectivities of plural samples 9 being carried.

FIG. 8 shows an arrangement of the automatic optical measurement system for measuring reflectivities of plural samples 9 being carried.

A carriage stage 10 for the samples 9 is preferably formed from a diffusion surface such that an unwanted light reflection may not occur.

While the samples 9 are carried one after another, an intensity of light is measured at a moment between passages of the individual samples 9. This intensity of light is defined as M1. Calculating M1·F gives R1, which means an intensity of light assumed to be obtained if the reference reflection plate 8 were actually set in place.

The intensity of light to be sensed at the passage of the sample 9 is defined as M1+S1. Then, S1 is determined by calculating (M1+S1)−M1.

A reflectivity of the sample 9 corrected for light intensity can be obtained by calculating S1/R1.

As described above, even if the light source is varied in the intensity of light, an accurate measurement may be taken on the reflectivity of the sample 9 without actually setting the reference reflection plate 8 in place.

What is claimed is:

1. An automatic optical measurement method including a light projecting portion and a light receiving portion disposed in close adjacency to each other for taking measurement on light projected from the projecting portion onto a sample and thence reflected, wherein a transparent or translucent member is fixed in place between the sample, and the light projecting and receiving portions for reflecting a part of the light projected from the light projecting portion into the light receiving portion, comprising determining a ratio between a measurement of an intensity of light reflected by the transparent or translucent member and a measurement of intensity of light reflected by a reference, by using a measurement of intensity of light reflected from the transparent or translucent member and a measurement of intensity of light taken with the reference set in place and estimating an intensity of light assumed to be obtained if the reference were set in place during a sample measurement, by using a measurement of intensity of light taken from the transparent or translucent member and the ratio thus determined, so as to correct the measurement of intensity of light reflected from the sample.

2. An automatic optical measurement method as claimed in claim 1, wherein the transparent or translucent member is tightly adhered to the light projecting and receiving portions.

3. An automatic optical measurement method as claimed in claim 1, wherein the transparent or translucent member is spaced away from the light projecting and receiving portions.

* * * * *